(12) United States Patent
Belbruno et al.

(10) Patent No.: US 9,034,262 B2
(45) Date of Patent: May 19, 2015

(54) MOLECULARLY IMPRINTED POLYMER SENSOR SYSTEMS AND RELATED METHODS

(75) Inventors: Joseph J. Belbruno, Hanover, NH (US); Ursula J. Gibson, Etna, NH (US); Jane E. G. Lipson, Hanover, NH (US); Martin N. Wybourne, Hanover, NH (US)

(73) Assignee: The Trustees of Dartmouth College, Hanover, NH (US)

( * ) Notice: Subject to any disclaimer, the term of this patent is extended or adjusted under 35 U.S.C. 154(b) by 1377 days.

(21) Appl. No.: 12/304,943

(22) PCT Filed: Jun. 14, 2007

(86) PCT No.: PCT/US2007/071231
§ 371 (c)(1),
(2), (4) Date: Jul. 6, 2009

(87) PCT Pub. No.: WO2008/045596
PCT Pub. Date: Apr. 17, 2008

(65) Prior Publication Data
US 2010/0039124 A1    Feb. 18, 2010

Related U.S. Application Data

(60) Provisional application No. 60/814,021, filed on Jun. 15, 2006.

(51) Int. Cl.
*G01N 15/06*    (2006.01)
*G01N 33/00*    (2006.01)
*G01N 27/12*    (2006.01)
*B82Y 15/00*    (2011.01)

(52) U.S. Cl.
CPC .............. *G01N 27/127* (2013.01); *B82Y 15/00* (2013.01); *G01N 27/126* (2013.01); *G01N 2600/00* (2013.01)

(58) Field of Classification Search
USPC ................ 435/7.1, 287.2; 205/777.5; 422/50, 422/68.1, 82.01, 82.02; 436/43, 149
See application file for complete search history.

(56) References Cited

U.S. PATENT DOCUMENTS

| | | | |
|---|---|---|---|
| 6,773,926 B1 * | 8/2004 | Freund et al. | 436/149 |
| 6,807,842 B2 | 10/2004 | Williams et al. | |
| 2002/0015690 A1 * | 2/2002 | Green et al. | 424/78.32 |
| 2004/0126814 A1 * | 7/2004 | Singh et al. | 435/7.1 |
| 2005/0070802 A1 * | 3/2005 | Peters et al. | 600/459 |
| 2013/0040399 A1 | 2/2013 | Belbruno et al. | |
| 2014/0220706 A1 | 8/2014 | BelBruno | |

OTHER PUBLICATIONS

Hedborg et al. (1992) "Some studies of molecularly-imprinted polymer membranes in combination with field-effect devices," *Sens. Actuators. A. Phys.* (37-38):796-799.

(Continued)

*Primary Examiner* — Brian J Sines
(74) *Attorney, Agent, or Firm* — Lathrop & Gage LLP

(57) ABSTRACT

A molecularly imprinted polymer (MIP) sensor including a substrate, two or more electrodes, a conductive layer applied to the substrate and a molecularly imprinted polymer layer applied to the conductive layer is disclosed herein The MIP sensor may form part of an MIP sensor system that can be used to detect and quantify target molecules.

20 Claims, 4 Drawing Sheets

(56) References Cited

OTHER PUBLICATIONS

International Search Report with Written Opinion corresponding to International Patent Application No. PCT/US2007/071231, mailed May 7, 2008.

Kriz et al. (1996) "Introduction of molecularly imprinted polymers as recognition elements in conductometric chemical sensors," *Sensors and Actuators B.* 33:178-181.

Matsui et al. (2004) "Composite of Au Nanoparticles and Molecularly Imprinted Polymer as a Sensing Material," *Anal. Chem.* 76:1310-1315.

Suedee et al. (2006) "Molecularly imprinted polymer-modified electrode for on-line conductometric monitoring of haloacetic acids in chlorinated water," *Analytica Chimica Acta.* 569(1-2):66-75.

Wulff et al. (1972) "The use of polymers with enzyme-analogous structures for the resolution of racemates," *Angew. Chem. Int. Ed.* 11:341.

Yoshimi et al. (2001) "'Gate effect' of thin layer of molecularly-imprinted poly(methacrylic acid-co-ethyleneglycol dimethacrylate)," *Sensors and Actuators B.* 73:49-53.

Zayats et al. (2002) "Imprinting of specific molecular recognition sites in inorganic and organic thin layer membranes associated with ion-sensitive field-effect transistors," *Tetrahedron.* 58:815-824.

\* cited by examiner

MOLECULARLY IMPRINTED POLYMER SENSOR SYSTEMS AND RELATED METHODS

RELATED APPLICATIONS

This application claims the benefit of priority to commonly-owned and U.S. Provisional Patent Application No. 60/814,021, filed 15 Jun. 2006, which is incorporated herein by reference.

BACKGROUND

Molecularly imprinted polymers (MIPs) are polymeric materials containing microscale cavities or imprints of defined shape. To create the imprints, target molecules are introduced into a solution containing polymerizable molecules that bind to the target molecules. Next, reaction conditions are changed, or crosslinking reagents are added to the solution, to cause the polymerizable molecules to form a solid polymer matrix in which the target molecules are immobilized. Finally, the target molecules are removed from the polymer matrix to form imprints having a particular shape. The MIP thus formed is able to selectively bind molecules that match the imprint shape with a lock-and-key-type interaction, when exposed to an environment containing a mixture of compounds.

The most common devices for detecting and quantifying molecules bound to an MIP utilize optical techniques, such as infrared, ultraviolet or visible spectroscopy; chemiluminescence, fluorescence or phosphorescence; or various forms of atomic microscopy. Most of these techniques require large-scale, expensive and technically-complex instrumentation. Analysis of MIPs, using such instruments, is therefore a time-consuming and costly process that is limited to those locations where the instruments are housed. When speed and portability are important because a molecule of interest may decompose or present a hazard, as occurs with many physiologically active compounds, these optical techniques are too slow and awkward to provide meaningful results.

Other detection and quantification devices utilize changes in resistance or capacitance to detect and/or quantify target molecules bound to an MIP. For example, U.S. Pat. No. 6,807,842 discloses a molecular recognition semiconductive polymer sensor system. The system contains carbon or copper doped polymers which are present as a non-imprinted reference polymer and one or more MIP(s). Sampling of an environment with the disclosed system leads to swelling of both the reference polymer and MIP due to absorption of interferents (molecules in the test environment other than target molecules) and target molecules. In particular, the reference polymer absorbs interferents and target molecules into the polymer matrix, whereas the MIP absorbs interferents, but target molecules occupy void spaces provided by the imprints. Thus, target molecules do not contribute to swelling of the MIP. The electrical resistance, which is directly related to distance between dopant atoms, changes in response to the swelling, and the presence and concentration of target molecules in the test environment is determined by the difference in resistance between the reference polymer and the MIP.

There are, however, a number of shortcomings associated with the use of doped polymer composites of the type described above. For example, some dopants, particularly metals, may not be chemically inert, and dopants may slow the release of bound target molecules so that a sensor may not be used for multiple tests in rapid succession or for continuous real-time monitoring of target molecule concentration. Additionally, it is difficult to ensure an even distribution of dopant atoms throughout the polymer matrix during formation of the MIP, and uncontrollable variations in composition make it difficult to reliably reproduce the performance characteristics of the sensors. Further, the repetitious application of electrical current directly to the polymer causes rapid decomposition.

SUMMARY

The present instrumentalities advance the art and overcome the problems outlined above by providing systems and methods useful for capturing, isolating, detecting and quantifying target molecules.

In one embodiment, a molecularly imprinted polymer (MIP) sensor includes a substrate; two or more electrodes; a conductive layer applied to the substrate and contacting the two or more electrodes; and a molecularly imprinted polymer layer applied to the conductive layer.

In one embodiment, a molecularly imprinted polymer sensor system includes a molecularly imprinted polymer (MIP) sensor having an undoped MIP layer that interfaces with a conductive layer; a power supply for supplying current to the conductive layer; and a resistance measurement device.

In one embodiment, a method of detecting a target molecule includes exposing a molecularly imprinted polymer (MIP) sensor, having an undoped MIP layer that interfaces with a conductive layer, to an environment to be tested for the presence of the target molecule; supplying current to the conductive layer of the MIP sensor; and measuring resistance of the MIP sensor to detect the presence of the target molecule. The method may further include quantifying the resistance to determine a concentration of the target molecule.

DETAILED DESCRIPTION

As used herein, a "non-conductive" material is one that does not substantially conduct electricity. For example, non-conductive materials typically have electrical conductivity values between $1 \times 10^{-5}$ $S \cdot m^{-1}$ and $1 \times 10^{-18}$ $S \cdot m^{-1}$, and more typically between $1 \times 10^{-8}$ $S \cdot m^{-1}$ and $1 \times 10^{-15}$ $S \cdot m^{-1}$ (e.g., glass, $10^{-10}$-$10^{-14}$ $S \cdot m^{-1}$; rubber, $10^{-13}$ $S \cdot m^{-1}$). On the other hand, "conductive" materials, which readily conduct a flow of electrons, typically have electrical conductivity values between $1 \times 10^6$ $S \cdot m^{-1}$ and $1 \times 10^8$ $S \cdot m^{-1}$, and more typically between $1 \times 10^6$ $S \cdot m^{-1}$ and $1 \times 10^7$ $S \cdot m^{-1}$ (e.g., gold; $45 \times 10^6$ $S \cdot m^{-1}$; silver, $63 \times 10^6$ $S \cdot m^{-1}$; platinum, $9.6 \times 10^6$ $S \cdot m^{-1}$; palladium, $9.5 \times 10^6$ $S \cdot m^{-1}$; copper, $59 \times 10^6$ $S \cdot m^{-1}$; aluminum, $38 \times 10^6$ $S \cdot m^{-1}$). Materials having electrical conductivity values falling between the ranges defined above are "semiconductive" materials. Semiconductive materials may be used in some embodiments of the present systems.

Figure 1:
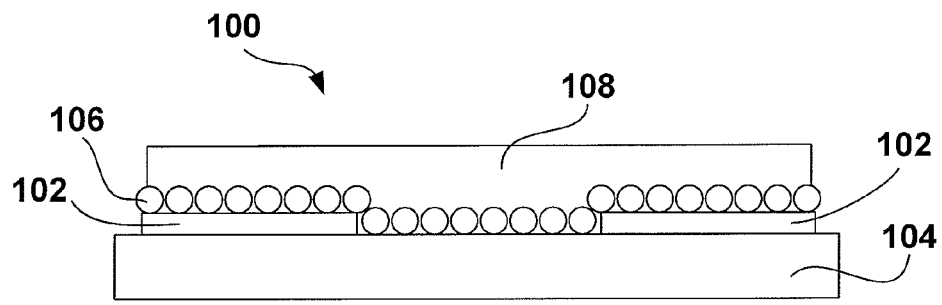
FIG. 1 shows a cross-sectional view of one exemplary MIP sensor, according to an embodiment.

FIG. 1 shows a cross-sectional view of one exemplary MIP sensor 100. MIP sensor 100 may, for example, be circular, spherical, square, rectangular or irregular in shape. Typical dimensions for sensor 100 are between about 1-10 mm. It will, however, be appreciated that larger sensors may be fabricated as desired. MIP sensor 100 includes two or more electrodes 102 applied, e.g., by chemical vapor deposition (CVD), to a substrate 104. In one example of fabrication, electrodes 102 are formed of copper, while substrate 104 is typically an insulating material, such as glass, rubber, sapphire, or a nitride or carbide ceramic. A conductive layer 106 comprising metallic nanoparticles is deposited over electrodes 102 and substrate 104. Gold, silver, platinum, palladium, copper or aluminum particles, having sizes in a range from about 2-50 nm, are used to form conductive layer 106, which has a thickness between about 10-50 nm, and preferably between about 10-30 nm. As shown, conductive layer 106 represents a monolayer; however, conductive layer 106 may contain one, two, three or more particle layers. The gold, silver, platinum, palladium, copper or aluminum particles are spin or drop coated onto substrate 104. An MIP 108 is deposited over conductive layer 106. MIP 108 may be prepared according to the general methods described by Wulff, G. and Sarhan, A., "Use of Polymers with Enzyme-Analogous Structures for the Resolution of Racemates," *Angewandte Chemie International Edition* 11(2), 341-346 (1972). Suitable MIPs 108 may, for example, be formed of nylon, saran, acrylamide, polyesters, polyethers, polyurethanes, polystyrenes, and block co-polymers and/or physical mixtures thereof. MIP 108 may be applied using a spin casting technique which involves dissolving the polymer and target molecule, at concentrations of 10-30% and 5-15% by weight of the solution respectively, in a volatile solvent, such as formic acid. The volatile solvent is applied over the previously deposited conductive layer 106 on a spinning substrate 104; the solvent rapidly evaporates when contacted with the surface leaving a solid polymer matrix in which the target molecule is immobilized. The thickness of the polymer matrix is dependent upon the rotation speed, spray parameters and the weight percent of polymer in the casting solution. Typical MIP layers 108 have thicknesses between about 100 nm and about 5 μm. Target molecules may be removed from the polymer matrix by washing with water or by soaking the MIP in a suitable solution, such as acetic acid, to dissolve the target molecules.

Figure 2:
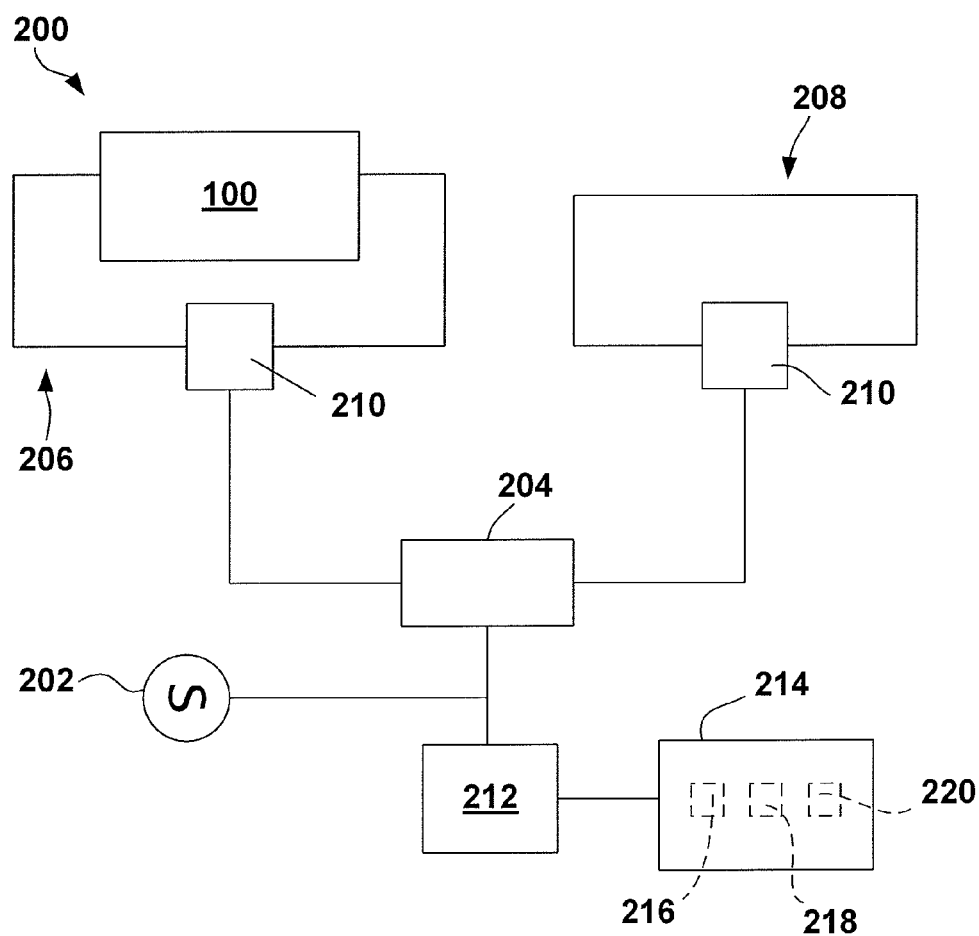
FIG. 2 shows a block diagram of one exemplary MIP sensor system for detecting a target molecule, according to an embodiment.

FIG. 2 shows a block diagram of one exemplary system 200 for detecting a target molecule. System 200 includes a power supply 202 which supplies current to a circuit 204. Circuit 204 feeds current to test loop 206 and reference loop 208, which each contain a resistance measurement device 210. Resistance measurement device 210 may, for example, be an ohm meter, oscilloscope, or any other suitable device to measure resistance. Test loop 206 connects to electrodes 102 on MIP sensor 100, and reference loop 208 may include a similarly constructed non-imprinted reference polymer sensor, or may not bear any load. A reference polymer is a polymer similar to the MIP being used to detect a target molecule, but lacking imprints. Signals from resistance measurement devices 210 are transmitted through circuit 204 to an analogue to digital converter 212, which may be interfaced with a computer 214 having a microprocessor 216, memory 218 and software 220.

Figure 3:
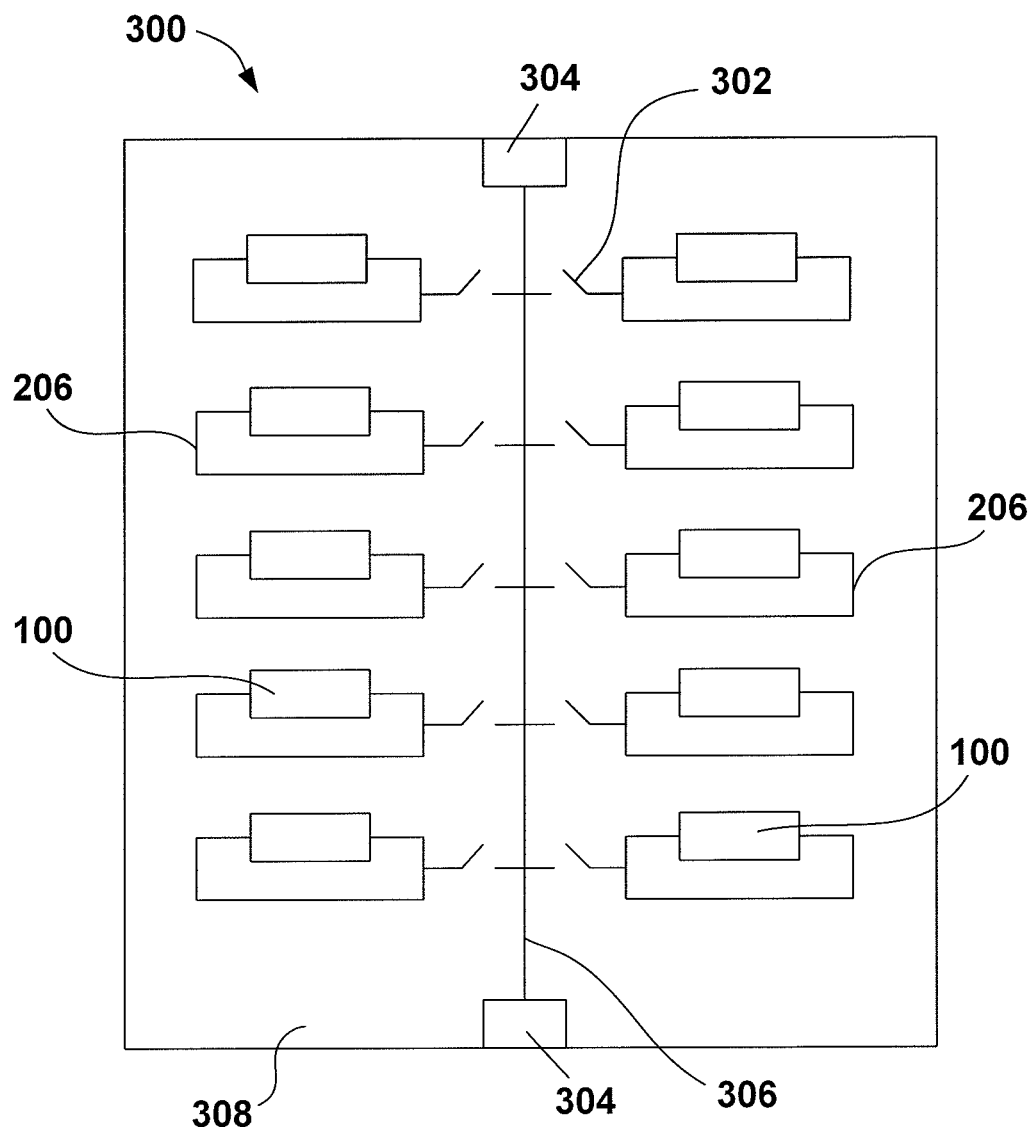
FIG. 3 shows a schematic of one exemplary sensor array incorporating multiple MIP sensors, according to an embodiment.

Each MIP 108 has imprints of one or more types of target molecules. In one example of operation, shown in FIG. 3, a sensor array 300 includes a plurality of MIP sensors 100, and optionally one or more non-imprinted reference polymer sensors, arranged in a pattern such that the relative positions of the MIP sensors within the array or pattern correlate with their identities, i.e., the identities of the target molecules used to create them. Each position or address within the array may comprise an imprint of a single target molecule, or imprints of a plurality of different target molecules, depending upon the application. Moreover, the entire array or pattern may comprise unique sensors, or may include redundant sensors, depending upon the application. Screening of individual addresses, rows, columns or blocks may be controlled by a series of switches 302. Electricity is supplied to sensor array 300 through a pair of electrical contacts 304, which connect to an electrical trace 306. Electrical trace 306 is, for example, applied to chip 308 using photolithographic techniques known in the art. As shown in FIG. 2, resistance measurement devices 210 may be incorporated into test loops 206. Alternatively, a resistance measurement device 210 may be connected to chip 308 by way of an electrical contact 304, which may be the same contact used for power source 202 or it may be a different contact. It will be appreciated that a wide variety of sensor arrays 300, differing from one another in the number of MIP sensors 100 and the arrangement thereof, fall within the scope of this disclosure.

Figure 4:
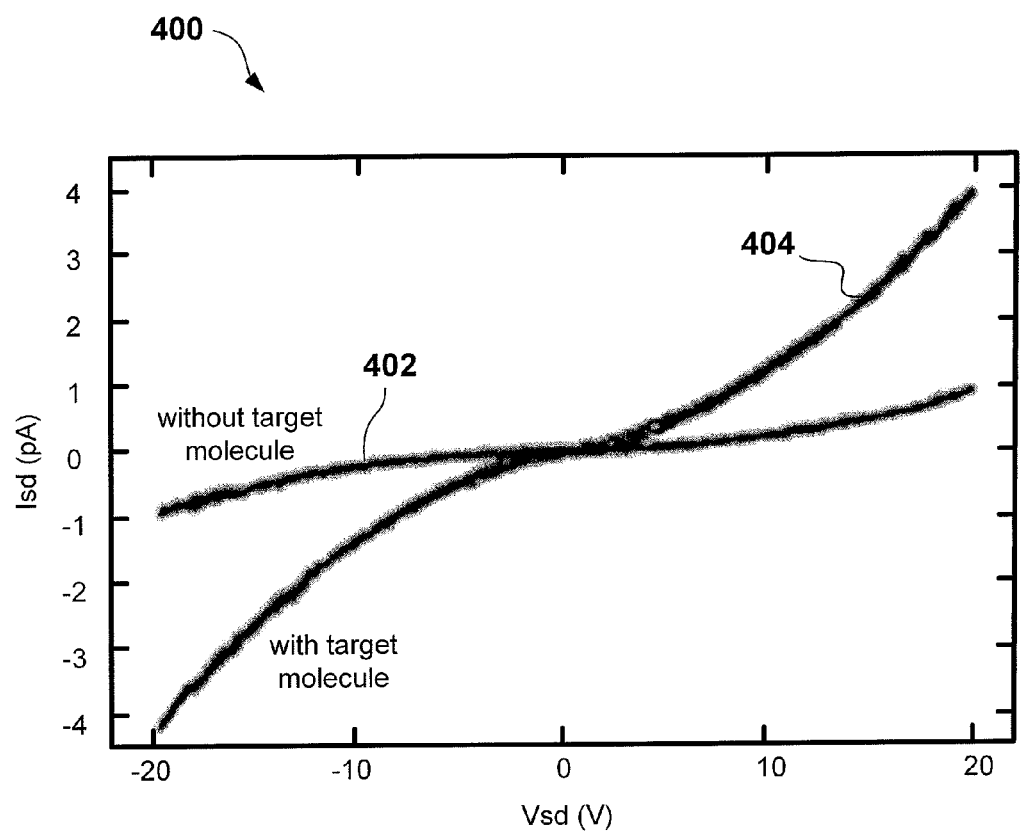
FIG. 4 shows a current versus voltage plot illustrating a response of an MIP sensor with and without binding of a target molecule, according to an embodiment.

FIG. 4 shows a current versus voltage (IV) plot 400 illustrating a response of MIP sensor 100 to the absence 402 and presence 404 of target molecules. In this particular example, MIP sensor 100 includes a gold conductive layer 106 and an L-glutamine imprinted nylon polymer 108. As shown, the slopes of the IV curves are inversely related to resistance. Prior to binding of target molecules to MIP sensor 100, the slope of IV curve 402 is approximately zero. After binding of target molecules to MIP sensor 100, the slope of IV curve 404 has shifted to a more positive value, indicating that resistance decreases when target molecules are bound to MIP layer 108. Without being constrained by theory, it is believed that incorporation of target molecules into the MIP layer 108 changes the electronic environment of the conductive layer 106, so that resistivity decreases and current increases.

Upon reading and fully appreciating this disclosure, those skilled in the art will recognize that exact structural identity between a molecule and an imprint may not be necessary for binding to an MIP 108. For example, an MIP 108 formed with a given target molecule may bind a particular class of molecules having similar structure and functionality, or a macromolecule having a structural portion matching the imprint may bind to the MIP. It may therefore be possible to isolate and identify new molecules having a particular structural feature in common with the target molecule.

Sensors of the type described herein are useful, for example, in the detection of pollutants; explosives; biowarfare agents; hazardous chemicals, e.g., biocides, insecticides, carcinogens, mutagens; and biological markers, e.g., proteins, cholesterol, blood plasma levels of pharmaceuticals, hormones, steroids, illicit chemical substances and the like.

Figure 5:
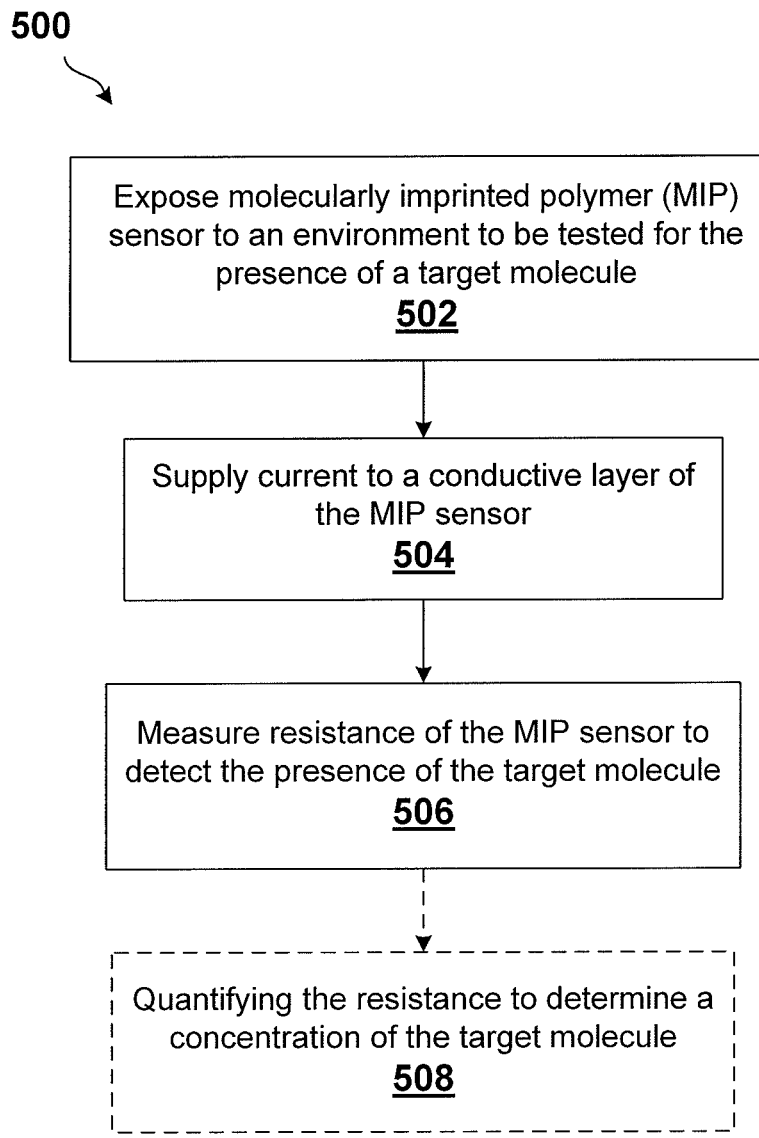
FIG. 5 is a block diagram illustrating exemplary steps for the detection of a target molecule using an MIP sensor system, according to an embodiment.

FIG. 5 is a block diagram 500 illustrating steps for the detection of a target molecule using an MIP sensor system 200. In step 502, an MIP sensor 100 is exposed to an environment to be tested for the presence of a target molecule. In steps 504 and 506, current is supplied to conductive layer 106 of MIP sensor 100 and resistance of MIP sensor 100 is measured to detect the presence of the target molecule. In optional step 508, the resistance may be quantified to determine a concentration of the target molecule. In an example of step 508, microprocessor 216 of computer 214 may access a look-up table containing information on MIP material and/or thickness, conductive layer material and/or thickness, target molecule, resistance and concentration. In another example of step 508, microprocessor 216 may execute software 220 that evaluates the measured resistance and sensor system parameters to determine target molecule concentration.

In another embodiment, a reference sensor may also be exposed to the environment being tested for the presence of the target molecule, and the resistance of the reference sensor may be measured. A comparison between the resistance of the reference sensor and the resistance of MIP sensor 100 may provide a more accurate determination of the presence of a target molecule than when the MIP sensor is used alone. It is also possible to quantify the difference in resistance between the reference sensor and the MIP sensor to determine a concentration of target molecules.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall there between.

What is claimed is:

1. A molecularly imprinted polymer sensor comprising:
an insulating substrate, and
at least two electrodes, and
a layer of metallic nanoparticles disposed on said substrate and in contact with said electrodes, and
a molecularly imprinted polymer layer disposed on said layer of metallic nanoparticles,
wherein said electrodes are disposed between said substrate and said layer of metallic nanoparticles.

2. The molecularly imprinted polymer sensor of claim 1, wherein said substrate is selected from the group consisting of glass, rubber, sapphire, a nitride ceramic and a carbide ceramic.

3. The molecularly imprinted polymer sensor of claim 1, wherein said metallic nanoparticles have diameters ranging from 2-50 nanometers.

4. The molecularly imprinted polymer sensor of claim 3, wherein said nanoparticles are selected from the group consisting of gold, silver, platinum, palladium, copper and aluminum.

5. The molecularly imprinted polymer sensor of claim 1, wherein said layer of metallic nanoparticles has a thickness between 10-50 nanometers.

6. The molecularly imprinted polymer sensor of claim 1, wherein said layer of metallic nanoparticles has a thickness between 10-30 nanometers.

7. The molecularly imprinted polymer sensor of claim 1, wherein said molecularly imprinted polymer layer comprises a polymer selected from the group consisting of nylon, saran, acrylamide, polyesters, polyethers, polyurethanes, polystyrenes and block co-polymers thereof.

8. The molecularly imprinted polymer sensor of claim 1, wherein said molecularly imprinted polymer layer has a thickness between 100 nanometers and 5 micrometers.

9. A molecularly imprinted polymer sensor system comprising:
a molecularly imprinted polymer sensor comprising
an insulating substrate, and
at least two electrodes, and
a layer of metallic nanoparticles, the layer of metallic nanoparticles being disposed on said substrate and in contact with said electrodes,
a molecularly imprinted polymer layer disposed on said layer of metallic nanoparticles,
wherein said electrodes are disposed between said substrate and said layer of metallic nanoparticles
a power supply for supplying current to said layer of metallic nanoparticles, and
a resistance measurement device connected to said electrodes.

10. The molecularly imprinted polymer sensor system of claim 9, wherein said metallic nanoparticles have diameters ranging from 2-50 nanometers.

11. The molecularly imprinted polymer sensor system of claim 10, wherein said nanoparticles are selected from the group consisting of gold, silver, platinum, palladium, copper and aluminum.

12. The molecularly imprinted polymer sensor system of claim 9, wherein said layer of metallic nanoparticles has a thickness between 10-50 nanometers.

13. The molecularly imprinted polymer sensor system of claim 9, wherein said layer of metallic nanoparticles has a thickness between 10-30 nanometers.

14. The molecularly imprinted polymer sensor system of claim 9, wherein said molecularly imprinted polymer layer comprises a polymer selected from the group consisting of nylon, saran, acrylamide, polyesters, polyethers, polyurethanes, polystyrenes and block co-polymers thereof.

15. The molecularly imprinted polymer sensor system of claim 9, wherein said molecularly imprinted polymer layer has a thickness between 100 nanometers and 5 micrometers.

16. The system of claim 9, further comprising a reference sensor.

17. A method of detecting a target molecule comprising:
exposing a molecularly imprinted polymer sensor to an environment to be tested for the presence of said target molecule, said molecularly imprinted polymer sensor comprising;
an insulating substrate, and
at least two electrodes, and
a layer of metallic nanoparticles disposed on said substrate and in contact with said electrodes, and
a molecularly imprinted polymer layer disposed on said layer of metallic nanoparticles,
wherein said electrodes are disposed between said substrate and said layer of metallic nanoparticles, and
said method further comprising supplying current to said layer of metallic nanoparticles of said molecularly imprinted polymer sensor, and
measuring a resistance of the molecularly imprinted polymer sensor to detect said target molecule.

18. The method of claim 17 further comprising quantifying said resistance to determine a concentration of the target molecule.

19. The method of claim 17 further comprising: exposing a reference sensor, having a non-imprinted, undoped polymer layer that interfaces with a layer of metallic nanoparticles, to said environment to be tested for said target molecule; supplying current to said layer of metallic nanoparticles of said reference sensor; measuring a resistance of said reference sensor;
and comparing said resistance of said reference sensor to said resistance of said molecularly imprinted polymer sensor.

20. The method of claim 19 further comprising quantifying a difference between said resistance of said molecularly imprinted polymer sensor and said resistance of said reference sensor to determine a concentration of said target molecule.

\* \* \* \* \*